United States Patent
Hsu et al.

[11] Patent Number: 5,151,526
[45] Date of Patent: Sep. 29, 1992

[54] 4-[1-(1-NAPHTHALENYL)ETHYL]-1H-IMIDAZOLE, METHOD OF MAKING AND USE AS AN ANESTHETIC

[75] Inventors: Fu-Lian Hsu, Rockville; William P. Ashman, Bel Air, both of Md.

[73] Assignee: The United States of America as represented by the Secretary of the Army, Washington, D.C.

[21] Appl. No.: 739,650

[22] Filed: Aug. 2, 1991

Related U.S. Application Data

[63] Continuation of Ser. No. 607,405, Oct. 11, 1990, abandoned.

[51] Int. Cl.$^5$ .............................. C07D 233/58
[52] U.S. Cl. ............................................. 548/335
[58] Field of Search ..................... 548/335; 514/396

[56] References Cited

U.S. PATENT DOCUMENTS 4,639,464  1/1987  Karjalainen et al. ............... 548/335
4,891,431  1/1990  Yamamoto et al. ................ 548/335

FOREIGN PATENT DOCUMENTS 1242571  9/1989  Japan .

OTHER PUBLICATIONS

Lindgren et al., *J. Heterocyclic Chem.*, 17, pp. 679–683 (1980).

*Primary Examiner*—Floyd D. Higel
*Assistant Examiner*—Lenora Miltenberger
*Attorney, Agent, or Firm*—Anthony T. Lane; Edward Goldberg; Edward F. Costigan

[57] ABSTRACT

The chemical 4-[1-(1-naphthalenyl)ethyl]-1H-imidazole and a method of making the same.

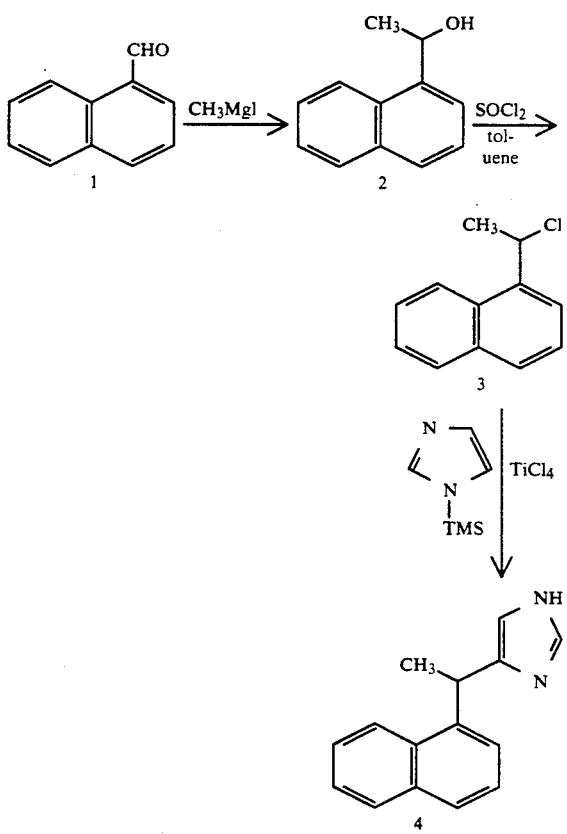

1 Claim, No Drawings

4-[1-(1-NAPHTHALENYL)ETHYL]-1H-IMIDAZOLE, METHOD OF MAKING AND USE AS AN ANESTHETIC

GOVERNMENTAL INTEREST

The invention described herein may be made, used or licensed by or for the Government for governmental purposes without the payment to me of any royalties thereon.

This application is a continuation of application Ser. No. 607,405, filed Oct. 11, 1990.

FIELD OF USE

The chemical known as 4-[1-(1-Naphthalenyl)ethyl]-1H-imidazole and a method of making the same.

BACKGROUND

Many selective adrenergic agonists have been shown to act in the central nervous system to reduce blood pressure and heart rate by stimulating selective adrenoceptors. In the art, this type of action has been used as the basis for developing new chemical agents which could be antihypertensive agents. One major concern of this type of compound if they are used as antihypertensive agents is the side effect - sedation. Thus, dissociation of sedative and cardiovascular actions has been a goal in the development of a great many new central acting $\alpha_2$-adrenoceptor agonists. A selective adrenergic agonist possessing either hypotensive or sedative action is a precursor for new antihypertensive agent or anesthetic agent, respectively.

The clinical uses of these latter compounds are very limited due to the dual actions: hypotensive and sedative effects, produced by this type of compounds. It is very clear that the development of a selective antihypertensive agent without sedative effect or vice versa would have the potential clinical applications. However, this type of compound is a very useful tool to study the adrenergic receptors subtypes of their pharmacological or anatomical aspect.

SUMMARY OF THE INVENTION

The chemical 4-[1-(1-Naphthalenyl)ethyl]-1H-imidazole and a method of making the same.

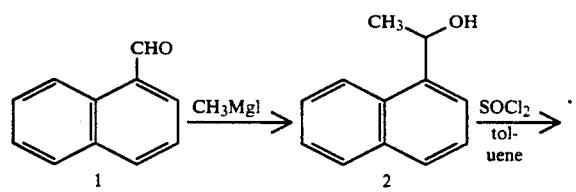

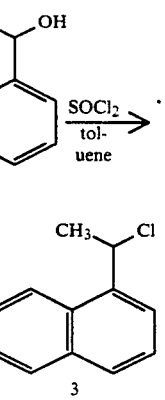

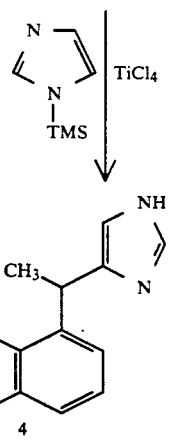

Synthesis of 4-[1-(1-Naphthalenyl)ethyl]-1H-imidazole. All reagents were purchased from Aldrich Chemical Co., Inc., Milwaukee, Wis., U.S.A.

1-(1-Naphthalyl)ethanol (2). To a solution of methylmagnesium iodide in ether which was prepared from magnesium turning (1.08 g, 44.4 mmol) and methyl iodide (2.75 ml, 44.2 mmol) in 100 ml of ether, were added a solution of 1-naphthaldehyde (1) (5.75 g, 36.8 mmol) in 10 ml of ether with cooling in an ice-water bath, then the resulting reaction mixture was stirred for 2 hours at room temperature. To this mixture was added 25 ml of 2N hydrochloric acid and then the organic layer was separated from the aqueous layer. The organic layer was washed with 50 ml of brine and dried over sodium sulfate. Evaporation of the solvent in vacuo gave 6.20 g (97%) of 2 as a viscous oil.

1-(1-Naphthalyl)ethyl chloride (3). A solution of 1-(1-naphthalyl)ethanol (6.34 g, 38.8 mmol) and thionyl chloride (5.37 ml, 73.6 mmol) in 65 ml of toluene was refluxed for 4 hours. The reaction mixture was evaporated to give the residue as an oil. The residue was dissolved in 150 ml of ethyl acetate, washed successively with 50 ml of water, 50 ml of saturated sodium bicarbonate and 50 ml of brine, and dried over sodium sulfate. The solvent was removed in vacuo to give 3(6.83 g, 97%) as an oil.

4-[1-(Naphthalenyl)ethyl]-1H-imidazole (4). To a solution of titanium tetrachloride (7.9 ml, 72.0 mmol) in 70 ml of chloroform was added a solution of 1-(trimethylsilyl)imidazole (10.5 ml, 71.6 mmol) in 70 ml of chloroform with cooling in an ice-water bath for 30 minutes. The resulting orange colored mixture was kept stirring for 30 minutes and then a solution of 3 (6.83 g, 36.8 mmol) in 35 ml of chloroform was added to the reaction mixture with cooling in an ice-water bath. The reaction mixture was kept stirring overnight. Water (150 ml) was added to the reaction mixture and the aqueous layer was separated and washed with methylene chloride. Then 150 ml of 2N sodium hydroxide was added to make aqueous layer basic which was extracted with chloroform. The combined organic layer was washed with brine, dried over sodium sulfate, and evaporated to give a solid which was recrystallized from methanol-methylene chloride-hexane yielding 4(1 56 g, 19.6%): mp 175.0-176.0 C; $^1$H NMR (CD$_3$OD, TMS)$\delta$ 8.16-7.25 (m, 7H), 7.57 (s, 1H), 6.74 (s, 1H), 4.95 (q, 1H, J=7.12 Hz), and 1.72 (d, 3H, J=7.12 Hz).

Analysis. Calculated for $C_{15}H_{14}N_2$: C, 81.05; H, 6 25; N, 12.60. Found: C, 81.20; H, 6.37; N, 12.68.

To a solution of 4(0.23 g, 1.03 mmol) in 3 ml of methanol was added 1.09 ml of 1N hydrochloric acid in methanol. Evaporation of the solvent gave the solid which was recrystallized from methanol-ether to give 0.20 g of the hydrochloride salt, 4.HCl: mp 120.0°–123.5°C.

Analysis. Calculated for $C_{15}H_{15}ClN_2$ C, 69.63; H, 5.84; N, 10.83 Found: C, 69.67; H, 5.72; N, 11.09.

METHOD OF USE

Four swine were surgically prepared with implanting of cathethers and probes for the measurement of respiratory, hemodynamic and MAC (Minimum Anethestic Concentration). After recovery from surgery (about two weeks), the swine were placed in a swine sling and the implanted probes and catherers were connected to recording equipment for monitoring of responses; and awake control measurements were made.

All doppler measurements were made with a 6 channel VF-1 Pulsed Doppler/Flow System (Crystal Biotech). A pulse doppler crystal was placed around either the circumflex or left anterior descending coronary arteries or both. A doppler thickening crystal was sutured to the left ventricle. These probes were used to measure coronary blood flow. Blood pressure and heart rate were transduced directly and are reported in mmHg.

After connection, each swine was then anesthesized by mask using isoflurane in oxygen and was connected to a semi-closed anesthesia circuit and allowed to breathe isoflurane spontaneously at approximately 1.8% in oxygen. MAC determination requires that 2 time points be used, one which is when the animal responds to a painful stimulus (in this case a clamp), the other when the animal does not respond. All values are averaged for these two points in time.

After determining the 1 MAC (control MAC) level for isoflurane, 4-[1-(1-naphthalenyl)ethyl]-1H-imidazole hydrochloride (4.HCl) was then given and MAC redetermined. The heart rate and MABP were recorded during the MAC determinations. The reduction in isoflurane requirement to maintain 1 MAC caused by 4.HCl was considered to be the anesthetic sparing effect and is reported as a fraction of MAC (Table 2). Example: If control MAC is 1.8% end-tidal isoflurane, and if after 4.HCl is given and MAC is reduced to 1.1% end-tidal isoflurane, then the MAC fraction is $(1.8-1.1)1.8 \times 100 = 38.9\%$ Therefore, 4.HCl can provide 38.9% of an anesthetic equivalent or is 38.9% anesthetic sparing. This anesthetic effect corresponds to the sedative effect.

The title compound was examined for its activity as inhibitor of platelet aggregation induced by epinephrine and compared to medetomidine.

TABLE 1

| Inhibition of primary and secondary phases of platelet aggregation induced by epinephrine (10–70 $\mu$M). | | |
|---|---|---|
| | $pIC_{50}$ ($\mu$M) | |
| Compound | with aspirin | without aspirin |
| Medetomidine | 5.48 ± 0.20 | 6.28 ± 0.17 |
| Present | 5.47 ± 0.16 | 5.83 ± 0.16 |

The sedative, anesthetic and hemodynamic effects of the title compound were examined using four Yucatan Mini swine as the model.

TABLE 2

| Sedative and hemodynamic effects of the 4-[1-(1-Naphthalenyl)ethyl]-1H-imidazole Hydrochloride. | | | |
|---|---|---|---|
| Dose ($\mu$g/Kg) | $MAC^a$ | $MABP^b$ | $HR^c$ |
| 1.0 | −9% | 16% | 113 |
| 10 | −16% | 58% | 84 |
| 100 | −39% | 62% | 75 |

[a] Miniumum Anesthetic Concentration (MAC) is a measure of the minimum amount of an anesthetic agent necessary to prevent a purposeful movement in response to a painful stimulus. Testing compounds in conjunction with a known anesthetic is required. In this study isofurane was used. To be able to quantify the sedative/anesthetic nature of the title compound, the compound was added to the known anesthetic, isoflurane and isoflurane was reduced until the same anesthetic level was achieved (1 MAC). If the known anesthetic can be removed entirely then the unknown is considered "fully" anesthetic or 1 MAC. If only a portion of the known anesthetic can be removed, (such as 50%) then the unknown is only capable of producing that proportion of the anesthesia (i.e., 0.5 MAC).
[b] The blood pressure (MABP) was measured in mmHg. The elevation is blood pressure (the peripheral effect) is best seen in this study by the maximum effect. The results were compared to the maximum values obtained after each drug dose to the maximum Control MAC values. The values were expressed as "Percent Change from Control MAC."
[c] Heart rate (HR) was recorded in bpm and was evaluated at the minimum values obtained during the drug runs for the reflex response to peripheral effects on blood pressure. The HR of awake control and Control MAC were 114 and 126, respectively.

Medical use of the subject compound: The results obtained from the $\alpha_2$-adrenergic receptor binding assay using platelet aggregation and the animal test for anesthetic and hemodynamic qualities indicated that the title compound was a selective anesthetic agent. Therefore the title compound has use as an anesthetic agent.

To a person of ordinary skill in the art to which this invention pertains many modifications and variations will suggest themselves, without the need for any undue experimentation to suit the needs of any given situation. Such modifications and variations are therefore within the scope of the present invention.

What is claimed:

1. 4-[1-(Naphthalenyl)ethyl]-1H-imidazole.

* * * * *